United States Patent
Lehmann et al.

Patent Number: 5,705,189
Date of Patent: Jan. 6, 1998

[54] THERMOPLASTIC MATERIAL FOR DRUG COATINGS WHICH DISSOLVE IN INTESTINAL JUICES

[75] Inventors: Klaus Lehmann, Rossdorf; Werner Hoess, Heusenstamm, both of Germany

[73] Assignee: Roehm GmbH Chemische Fabrik, Darmstadt, Germany

[21] Appl. No.: 521,738

[22] Filed: Aug. 31, 1995

[30] Foreign Application Priority Data

Aug. 31, 1994 [DE] Germany ............................ 9414065 U

[51] Int. Cl.⁶ .................. A61K 9/32; A61K 9/58
[52] U.S. Cl. .................. 424/451; 424/462; 424/463; 424/482; 424/497; 427/2.14
[58] Field of Search ........................ 424/462, 463, 424/482, 497, 451

[56] References Cited

U.S. PATENT DOCUMENTS 4,058,649  11/1977  Steiner ........................ 428/518

FOREIGN PATENT DOCUMENTS

| | | |
|---|---|---|
| 0 143 935 | 6/1985 | European Pat. Off. |
| 0 403 959 | 12/1990 | European Pat. Off. |
| 21 57435 | 6/1973 | Germany. |
| 2 091 203 | 7/1982 | United Kingdom. |
| WO 91/04017 | 4/1991 | WIPO. |

OTHER PUBLICATIONS

Chemical Abstracts, AN-87-015859/03, DE-3525767, Jan. 22, 1987.
Chemical Abstracts, AN-87-008884/02, DE-3524337, Jan. 8, 1987.

*Primary Examiner*—Thurman K. Page
*Assistant Examiner*—James M. Spear
*Attorney, Agent, or Firm*—Oblon, Spivak, McClelland, Maier & Neustadt, P.C.

[57] ABSTRACT

Thermoplastic materials which comprise a copolymer of
(A) 16 to 40 wt % of acrylic and/or methacrylic acid;
(B) 30 to 80 wt % of methyl acrylate; and
(C) 0 to 40 wt % of another alkyl ester of acrylic and/or methacrylic acid and perhaps conventional auxiliaries for drug coatings are suitable for the production of drug coatings which are soluble in intestinal juices, such as tablet coatings, dies, films, capsules, or multipart dosage units.

10 Claims, 2 Drawing Sheets

THERMOPLASTIC MATERIAL FOR DRUG COATINGS WHICH DISSOLVE IN INTESTINAL JUICES

BACKGROUND OF THE INVENTION

1. Field of the Invention

The present invention relates to thermoplastic materials for the production of drug coatings which are soluble in intestinal juices. The present invention also relates to pharmaceutical compositions in which an active agent is coated with or encapsulated in such a material. The present invention further relates to a method for delivering an active agent to the intestines comprising administering such a composition to a patient in need thereof.

2. Discussion of the Background

An important class of materials for drug coatings consists of copolymers of acrylic and/or methacrylic acid with lower alkyl esters of these acids. They are used in the form of solutions in organic solvents or as aqueous dispersions or redispersions for the production of pharmaceutical coatings. The processing of these solutions and dispersions is always connected with time- and energy-intensive drying steps for the evaporation of the water or solvent used. For the production of capsules, layers of the solutions or dispersions are dried on suitably shaped pins and removed; see West German Patent Nos. 2,157,435 and 3,524,337.

The plasticization of starch by heating with water and then processing into capsules by injection molding are also known. However, it was not possible, up to now, to produce capsules from the aforementioned acrylic polymers, which are soluble in intestinal juices, by an efficient thermal shaping method; see L. Eith et al., *Drug Der. Ind. Pharm.*, vol. 12 (11–13), pp. 2113–2126, 1986.

Furthermore, the enclosure of pharmaceutical molds in weldable films made of a material based on gelatin which can dissolve or disintegrate in the digestive tract and the oral application in this form are also known; see WO 91/04017. Organic solutions of pharmaceutically active substances and copolymers of methyl and/or ethyl esters of acrylic and methacrylic acid with low softening temperatures are dried in accordance with West German Patent No. 3,525,767; the residue is pulverized and pressed into tablets.

Thermoplastic material molding compositions based on a copolymer of 1 mole acrylic and/or methacrylic acid and 2.5–6 moles of at least one acrylate, which can be processed thermoplastically into films, deep drawn articles, injection moldings, pressing pieces or blow moldings, are known from European Patent No. B 143,935. The copolymers, however, contain, at most, 15 wt % carboxyl groups, which is not sufficient for the production of pharmaceutical mold coatings which are soluble in intestinal juices. Alkali-soluble films for hygienic and packaging purposes and adhesives and packaging parts are produced from the known copolymers.

Thus, there remains a need for thermoplastic materials useful for drug coatings and which dissolve in intestinal juices. There also remains a need for pharmaceutical compositions in which an active agent or drug is coated with such a material.

SUMMARY OF THE INVENTION

Accordingly, it is one object of the present invention to provide novel thermoplastic materials which are useful for drug coatings.

It is another object of the present invention to provide novel thermoplastic materials which are useful for drug coatings and which dissolve in intestinal juices.

It is another object of the present invention to provide pharmaceutical compositions which comprise a drug coated with such a thermoplastic material.

It is another object of the present invention to provide a method for delivering a drug to the intestines by administering such a pharmaceutical composition to a patient in need thereof.

These and other objects, which will become apparent during the following detailed description, have been achieved by the inventors' discovery that the known acrylic polymers, which are made up of 30 to 50 wt % methacrylic acid and, as the remainder, of ethyl acrylate or methyl methacrylate, are soluble in intestinal juices and can be processed from an aqueous dispersion or organic solution, but cannot be processed in the thermoplastic state without decomposition. Such copolymers begin to decarboxylate at temperatures above 120° C. and are then no longer soluble in intestinal juices.

Surprisingly, the goal of the present invention, to make available a thermoplastic material molding composition, which can be used by known thermoshaping methods for the production of pharmaceutical molds which can dissolve in intestinal juices, for example, capsules, has been achieved by the inventors' discovery that copolymers of:

(A) 16 to 40 wt % acrylic and/or methacrylic acid;
(B) 30 to 80 wt % methyl acrylate; and
(C) 0 to 40 wt % other alkyl esters of acrylic and/or methacrylic acid are suitable for this purpose. Drug coatings produced therefrom, perhaps with the addition of one or more conventional auxiliaries, are not soluble in gastric juice at a pH 1 to 2 and in intestinal juices or buffer solutions with pH values ≦5, but can dissolve well in intestinal juices at pH values of 5.5 to 8. Such materials can be processed without decomposition in the thermoplastic state.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
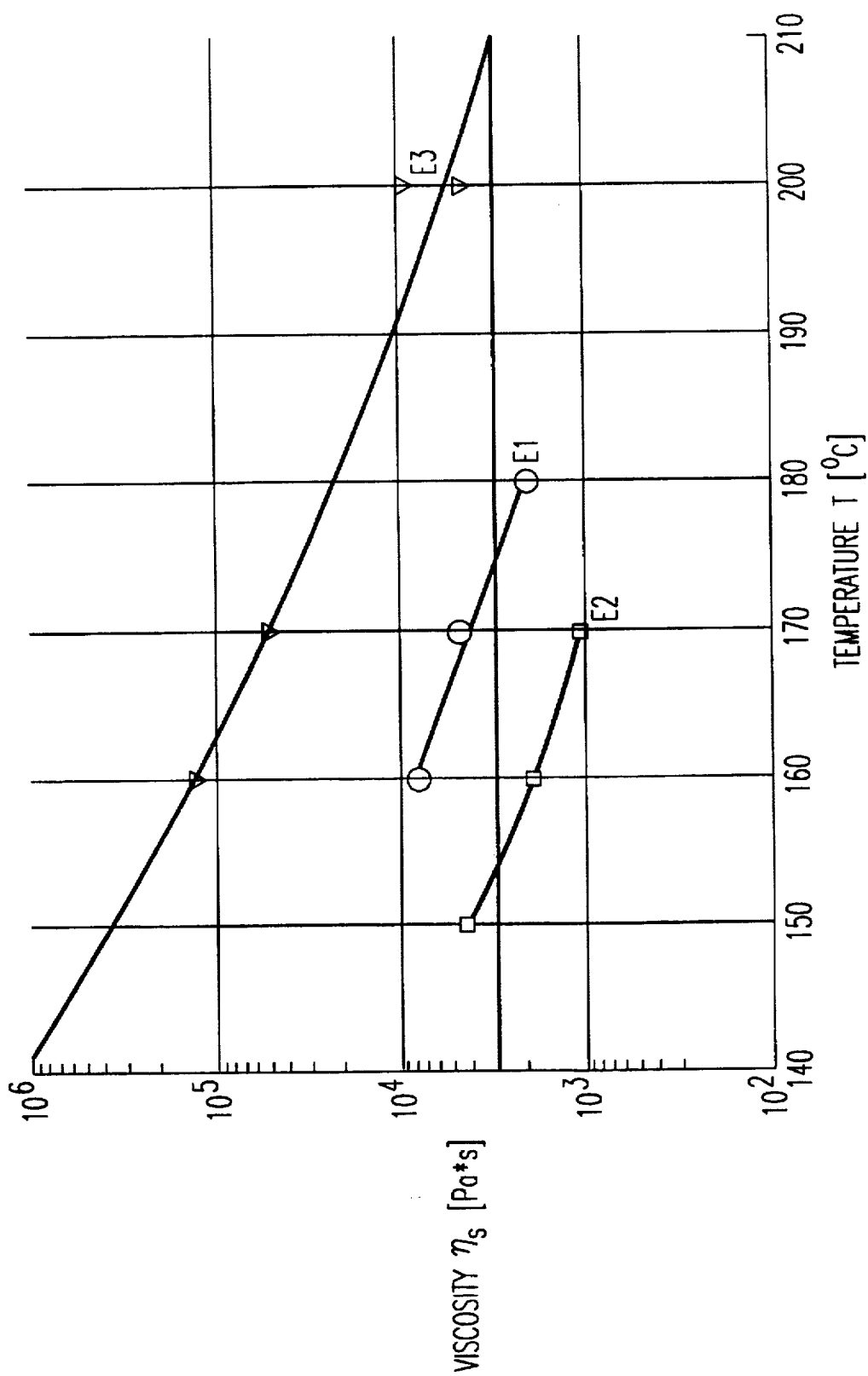
FIG. 1 shows the melt viscosities of copolymers E1, E2, and E3 as a function of the temperature of the polymer melt.

Thus, in a first embodiment, the present invention provides thermoplastic materials which are copolymers of:

(A) 16 to 40 wt %, preferably 20 to 30 wt %, of acrylic and/or methacrylic acid;
(B) 30 to 80 wt %, preferably 40 to 70 wt %, of methyl acrylate; and
(C) 0 to 40 wt %, preferably 5 to 30 wt %, of an alkyl ester of acrylic and/or methacrylic acid.

As noted above, the termoplastic material can take the form of a drug coating such as a shell, a capsule, or a capsule half. In a preferred embodiment, the coating takes the form of a capsule or capsule half.

Capsules or capsule halves can be produced, preferably with multiple impression dies, by the injection molding method from a melt of the copolymer at temperatures of 140° to 180° C. The injection molding method can also be used to coat preshaped drug cores with a polymer sheath. The cores are thereby held centered by means of auxiliary dies, which are withdrawn before the final filling of the mold cavity and before the solidification of the molding composition from the mold cavity. Other coating methods are described in WO 91/04017, which is incorporated herein by reference.

A film with a thickness of, for example, 0.1 to 1 mm can be produced from a melt of the molding composition in accordance with the invention by extrusion and perhaps smoothing in smoothing rolls. Such films can be used for pharmaceutical molds in various ways. In the thermoplastic state, capsule parts can be drawn at temperatures of 100° to 140 ° C. Known shaping methods in which the shaping is brought about by mechanical plugs, by excess or reduced pressure or by a combination of these means can be applied. After the cutting of the shaped capsule parts, the remaining film can once again be melted.

Molded articles made of the plastics in accordance with the invention can also be combined to form metering units with other molded articles made of soluble or insoluble materials, so as to control the dissolution of certain parts of the therapeutic system. Thus, limited dosages of one or more materials can be combined to form one metering unit in such a manner that individual dosages are released in certain sections of the gastrointestinal tract under defined conditions. The disintegration of the system into smaller parts, which can be excreted more easily, can be brought about also by jointly using molded articles which are soluble in intestinal juices.

Novel, efficient coating methods are possible because the film can be shaped and welded. For example, pressed tablet cores can be sealed and welded between two stretched films. Upon heating, the sheath shrinks tightly on the core.

The copolymer can be produced according to the usual methods of radical polymerization. Regulators, such as alkyl mercaptans, can be also used in order to attain a molecular weight (weight average) of 50,000 to 1,500,000 daltons (d). The melt viscosity of the isolated polymer or the finished molding composition is preferably in the range of 1,000 to 100,000 Pa.sec at 120°–145° C. and 1–5 mPa pressure, measured according to DIN 54811, Method B. The bulk polymerization of the monomers, for example, in a screw-type extruding machine, is an efficient method. Preferably, the copolymer is produced by emulsion polymerization in the aqueous phase in the presence of preferably anionic emulsifiers and is isolated by spray-drying, freeze-drying or by coagulation and dehydration.

Together with acrylic and/or methacrylic acid and methyl acrylate, other alkyl esters of acrylic and/or methacrylic acid, if desired, can also be used, in particular those with 1 to 8 carbon atoms in the alkyl radical, in quantities up to 40 wt %. The following are particularly suitable: ethyl, propyl, butyl and 2-ethylhexyl acrylate, and methyl, ethyl, propyl, and butyl methacrylate. In lesser quantities, it is also possible to use other ethylenically unsaturated, radically polymerizable monomers, such as hydroxyalkyl (meth)acrylates, so long as the presence of such monomers does not interfere with the good effects of the present thermoplastic materials.

The present thermoplastic material copolymer can be mixed with auxiliaries in the melt, which are common in drug coating compositions. Among these are plasticizers, such as citric acid esters, polyethylene glycols, fillers, dyes, pigments, preservatives, flavoring substances, active substances and mold-release agents, such as glycerol monostearate and distearate, mixtures of the two, and stearic acid and its metal salts.

The prepared molding composition is processed thermoplastically at temperatures of 120° to 180° C. For injection molding, a viscosity below 10,000 Pa.sec is desirable, which can generally be attained at temperatures of 140°–180° C.

In another embodiment, the present invention provides a method for delivering an active agent or drug to the intestines by administering a pharmaceutical composition, in which such an active agent or drug is coated with the present thermoplastic material, to a patient in need thereof. Typically, the pharmaceutical composition will be administered orally.

Other features of the invention will become apparent in the course of the following descriptions of exemplary embodiments which are given for illustration of the invention and are not intended to be limiting thereof.

EXAMPLES

Unless indicated otherwise, wt % means percent by weight based on the total weight of the monomers polymerized.

Example 1

A copolymer produced on a laboratory roll mill by the emulsion polymerization of a monomer mixture of 60 wt % methyl acrylate, 20 wt % methyl methacrylate, and 20 wt % methacrylic acid and subsequently spray-dried is melted at a roll temperature of 160° C. After the melt was homogenized, 6 wt % glycerol monostearate, based on the weight of the polymer, was added and mixed for several minutes. The rolled sheet was removed, broken, and comminuted in an impact pulverizer to form a powder with an average particle size of 0.2 mm.

The copolymer has a melt viscosity of 7,700 Pa.sec at 145° C./5 mPa.

To test the thermoplastic processability, the plastic powder was poured into the preliminary chamber of an injection mold and, at 170° C. under a pressure of 150 bar, injected through a 0.5-mm opening into the mold cavity. A fissure-free, bubble-free, slightly opaque, thin-wall drug capsule half was obtained, which was removed from the opened mold after cooling. It was possible to dissolve it in a buffer solution of pH 7.5 within 90 min.

Examples 2–5

In the same way, spray-dried emulsion polymers of the following compositions (in wt %):

Example 2: 80:20 methyl acrylate:methacrylic acid 1:1 core/shell structure with the monomer ratios 70:30/90:10

Example 3: 80:20 methyl acrylate:methacrylic acid 1:1 core/shell structure with the monomer ratios 90:10/70:30

Example 4: 40:25:35 methyl acrylate:ethyl acrylate:methacrylic acid

Example 5: 80:20 methyl acrylate:methacrylic acid core/shell structure, wherein only the core was produced with the addition of a regulator Example 6: 30:15:15:40 methyl acrylate:ethyl acrylate:butyl acrylate:methacrylic acid were processed into capsule halves with the addition of 2 wt %, based on the weight of the polymer, of glycerol monostearate (Example 4, only 1 wt %) as a mold-release auxiliary. In all cases, the capsule halves were soluble in buffer solutions of pH 7.5 within 90 min.

The copolymers have the following molecular weights $M_w$ (according to the GPC method, weight-average values) and melt viscosities $V_S$ at 145° C./5 mPa:

|            | $M_w$, d | $V_s$, Pa · sec |
|------------|----------|-----------------|
| Example 2: | —        | 23,000          |
| Example 3: | —        | 15,000          |
| Example 4: | 190,000  | 192,000         |
| Example 5: | 160,000  | 67,000          |
| Example 6: | 200,000  | 222,000         |

Examples 7–9

In the same manner, spray-dried emulsion polymers of methyl acrylate, methyl methacrylate, and methacrylic acid having the following weight ratios were processed into capsule halves:

Example 7: 40:40:20
Example 8: 60:20:20
Example 9: 60:25:15 with the addition of 3 wt %, based on the weight of the polymer, of glycerol monostearate as a mold-release agent. In Examples 8 and 9, an easier mold-release capacity and smoother capsule surfaces were attained with the use of 6 and, respectively, 5 wt % of the mold-release auxiliary. The capsule halves had a length of 16.5 mm, an outside diameter of 6.8 mm, a wall thickness of 0.5 mm and a weight of 146 mg.

The copolymers have approximately the following melt viscosities at 145° C./5 mPa:

Example 7: 85,000 Pa.sec
Example 8: 20,000 Pa.sec
Example 9: 16,000 Pa.sec

Test of the dissolution behavior of the capsules in accordance with Examples 8 and 9

Two capsule halves produced in accordance with Example 8 were filled with granules of a particle size of 3 mm and (for experimental purposes) closed watertight with cyanoacrylate adhesive. The filled capsule was first moved up and down 5 cm each at 30 strokes per minute in a beaker with 200 mL 0.1N HCl as artificial gastric juice. Within 2 hours at 37° C., the capsule wall became murky; no disintegration was observed, however, and no liquid was pressed into the interior. Subsequently, the liquid was replaced by a pH 7.5 phosphate buffer, and the movement was continued. The pH value was continuously measured and maintained constant by the addition of 0.5N NaOH, using a pH-stat. After 30 minutes, the capsule became very murky; at the same time, alkali consumption was observed. Within the next 50 minutes, the alkali consumption rose to 0.13 mL 0.5N NaOH, and the capsule opened up and released the granules. After a total of 120 minutes and an alkali consumption of 0.19 mL, the capsule was almost completely dissolved.

Two capsule halves produced according to Example 9 were filled with 60 mg bisacodyl pellets containing 5 wt % active substance and closed with cyanoacrylate adhesive. The capsule was, as described above, moved in 250 mL 0.1N HCl for 1 hour at 37° C., and did not exhibit any signs of disintegration. The extinction of 0.002 at 264 nm measured afterwards in the liquid shows that at most 0.3 wt % of the active substance diffused out. After changing the treatment liquid to pH 7.5 phosphate buffer and connection to a pH-stat, alkali consumption occurred already after 5 minutes. After 40 minutes, the capsule opened up and released the pellets. By the measurement of the extinction, it was possible to detect an active substance release of 92.3 wt %. Approximately half of the capsule material was dissolved by this point.

Investigations of Other Copolymers

Figure 2:
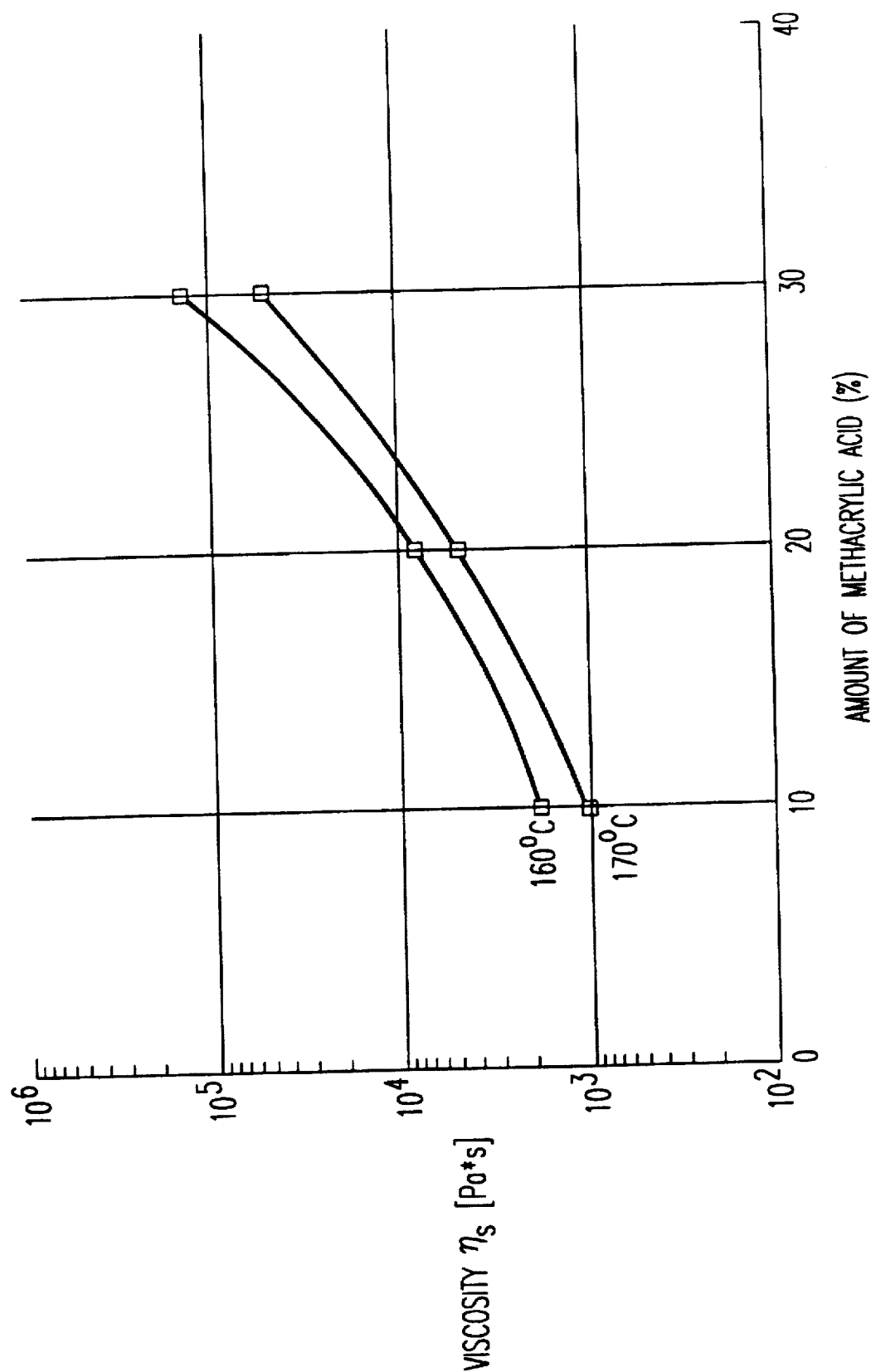
FIG. 2 shows the dependance of the melt viscosity at 160° C. and 170° C. on the amount of methacrylic acid in the copolymer.

For three emulsion polymers E1, E2, and E3 of methyl acrylate, methyl methacrylate, and methacrylic acid in the weight ratios:

E1: 60:20:20
E2: 65:25:10
E3: 50:20:30 the melt viscosities were measured as a function of the temperature of the polymer melt and plotted in FIG. 1. FIG. 2 shows the dependence of the melt viscosity at 160° or 170° C. on the methacrylic acid fraction in the copolymer.

This application is based on German Utility Model Application G 94 14 065.0 filed on Aug. 31, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by letters patent of the U.S. is:

1. A thermoplastic material for the production of drug coatings, which are soluble in intestinal juices, comprising a copolymer of:

(A) 16 to 40 wt % of acrylic and/or methacrylic acid;
(B) 30 to 80 wt % of methyl acrylate; and
(C) 0 to 40 wt % of another alkyl ester of acrylic and/or methacrylic acid;

wherein said copolymer has a melt viscosity in the range of 1000 to 100,000 Pa.sec at 120° to 145° C. and a weight average molecular weight of 50,000 to 1,500,000 d.

2. A method for the production of a drug capsule, comprising melting a thermoplastic material which comprises a copolymer of:

(A) 16 to 40 wt % of acrylic and/or methacrylic acid;
(B) 30 to 80 wt % of methyl acrylate; and
(C) 0 to 40 wt % of another alkyl ester of acrylic and/or methacrylic acid, to obtain a melt;
forming a film from said melt by extrusion; and
thermally shaping said film to form a capsule.

3. A method of delivering an active agent to the intestines, comprising administering to a patient in need thereof a pharmaceutical composition in which said active agent is coated with a thermoplastic material which comprises a copolymer of:

(A) 16 to 40 wt % of acrylic and/or methacrylic acid;
(B) 30 to 80 wt % of methyl acrylate; and
(C) 0 to 40 wt % of another alkyl ester of acrylic and/or methacrylic acid.

4. A weldable plastic film, comprising a thermoplastic material comprising a copolymer of:

(A) 16 to 40 wt % of acrylic and/or methacrylic acid;
(B) 30 to 80 wt % of methyl acrylate; and
(C) 0 to 40 wt % of another alkyl ester of acrylic and/or methacrylic acid;

wherein said copolymer has a melt viscosity in the range of 1000 to 100,000 Pa.sec at 120° to 145° C. and a weight average molecular weight of 50,000 to 1,500,000 d.

5. The weldable plastic film of claim 4, which is stretched in one or two dimensions.

6. A pharmaceutical composition, comprising an active agent coated with a thermoplastic material, wherein said thermoplastic material comprises a copolymer of:

(A) 16 to 40 wt % of acrylic and/or methacrylic acid;
(B) 30 to 80 wt % of methyl acrylate; and
(C) 0 to 40 wt % of another alkyl ester of acrylic and/or methacrylic acid;

wherein said copolymer has a melt viscosity in the range of 1000 to 100,000 Pa.sec at 120° to 145° C. and a weight average molecular weight of 50,000 to 1,500,000 d.

7. A drug capsule, comprising a thermoplastic material, said thermoplastic material comprising a copolymer of:

(A) 16 to 40 wt % of acrylic and/or methacrylic acid;
(B) 30 to 80 wt % of methyl acrylate; and
(C) 0 to 40 wt % of another alkyl ester of acrylic and/or methacrylic acid;

wherein said copolymer has a melt viscosity in the range of 1000 to 100,000 Pa.sec at 120° to 145° C. and a weight average molecular weight of 50,000 to 1,500,000 d.

8. A drug dosage unit, comprising one or more active substance dosages and at least one molded part comprising thermoplastic material, said thermoplastic material comprising a copolymer of:

(A) 16 to 40 wt % of acrylic and/or methacrylic acid;
(B) 30 to 80 wt % of methyl acrylate; and
(C) 0 to 40 wt % of another alkyl ester of acrylic and/or methacrylic acid;

wherein said copolymer has a melt viscosity in the range of 1000 to 100,000 Pa.sec at 120° to 145° C. and a weight average molecular weight of 50,000 to 1,500,000 d.

9. A method for coating a drug, wherein a thermoplastic material comprising a copolymer of:

(A) 16 to 40 wt % of acrylic and/or methacrylic acid;
(B) 30 to 80 wt % of methyl acrylate; and
(C) 0 to 40 wt % of another alkyl ester of acrylic and/or methacrylic acid is melted to obtain a melt and a drug coating is molded from said melt.

10. The method of claim 9, wherein said drug coating is molded from said melt by injection molding.

* * * * *